(12) United States Patent
Black et al.

(10) Patent No.: US 12,291,496 B2
(45) Date of Patent: May 6, 2025

(54) PROCESS AND APPARATUS FOR THE PREPARATION OF ALKYLENE GLYCOL

(71) Applicant: SHELL USA, INC., Houston, TX (US)

(72) Inventors: Jesse Raymond Black, Houston, TX (US); Peter Mervyn Wilkinson, Bangalore North (IN); Christopher Paul Emborsky, Houston, TX (US); Roel Guillaume Hubertus Leonardus Bastings, Amsterdam (NL); Benedict Ignatius Maria Ten Bosch, Amsterdam (NL)

(73) Assignee: SHELL USA, INC., Houston, TX (US)

( * ) Notice: Subject to any disclaimer, the term of this patent is extended or adjusted under 35 U.S.C. 154(b) by 0 days.

(21) Appl. No.: 18/740,657

(22) Filed: Jun. 12, 2024

(65) Prior Publication Data

US 2024/0400480 A1 Dec. 5, 2024

Related U.S. Application Data

(62) Division of application No. 17/293,788, filed as application No. PCT/EP2019/081815 on Nov. 19, 2019, now Pat. No. 12,054,450.

(30) Foreign Application Priority Data

Nov. 22, 2018 (EP) .................................... 18207673

(51) Int. Cl.
*C07C 29/10* (2006.01)
*B01D 3/00* (2006.01)
(Continued)

(52) U.S. Cl.
CPC ............ *C07C 29/106* (2013.01); *B01D 3/008* (2013.01); *B01D 3/20* (2013.01); *B01D 3/324* (2013.01)

(58) Field of Classification Search
CPC .......... C07C 29/06; B01D 3/008; B01D 3/20; B01D 3/324
See application file for complete search history.

(56) References Cited

U.S. PATENT DOCUMENTS

| 5,763,691 A | 6/1998 | Kawabe et al. |
| 7,453,014 B2 | 11/2008 | Harmsen et al. |
(Continued)

FOREIGN PATENT DOCUMENTS

| CN | 107648999 A | 2/2018 |
| GB | 2107712 A | 5/1983 |

OTHER PUBLICATIONS

International Search Report and Written Opinion received for PCT Patent Application No. PCT/EP2019/081815, mailed on Feb. 7, 2020, 09 pages.
(Continued)

*Primary Examiner* — Jafar F Parsa
(74) *Attorney, Agent, or Firm* — SHELL USA, INC.

(57) ABSTRACT

A process for the preparation of an alkylene glycol from an alkene comprising steps of: a) supplying a gas composition to an alkylene oxide absorber through a gas inlet, the absorber comprising an absorption section and a sump, and allowing the gas composition to pass upwards; b) supplying a lean absorbent to the top of the absorption section and allowing the lean absorbent to pass downwards; c) intimately contacting the gas composition with lean absorbent in the absorption section in the presence of one or more catalysts that promote carboxylation and hydrolysis; and d) withdrawing fat absorbent from the absorption section and passing the fat absorbent and any liquid condensate through the sump, wherein the sump comprises one or more baffles that define a flow pathway from a sump inlet to a sump outlet between the one or more baffles.

7 Claims, 3 Drawing Sheets

(51) Int. Cl.
*B01D 3/20* (2006.01)
*B01D 3/32* (2006.01)

(56) References Cited

U.S. PATENT DOCUMENTS

| | | |
|---|---|---|
| 8,063,256 B2 | 11/2011 | Van Kruchten |
| 9,365,535 B2 | 6/2016 | Van Kruchten et al. |
| 10,279,280 B2 | 5/2019 | Wilkinson et al. |

OTHER PUBLICATIONS

Office Action Received for Chinese Application No. 201980073267.4, Mailed on Feb. 21, 2023, 18 Pages (12 Pages of English Translation and 6 Pages of Official Copy).

PROCESS AND APPARATUS FOR THE PREPARATION OF ALKYLENE GLYCOL

CROSS REFERENCE TO RELATED APPLICATIONS

This is a divisional application of U.S. patent application Ser. No. 17/293,788 filed on 13 May 2021 which is a national stage application of International Application No. PCT/EP2019/081815, filed 19 Nov. 2019, which claims benefit of priority to European Patent application 18207673.7, filed 22 Nov. 2018.

FIELD OF THE INVENTION

The present invention relates to a process and an apparatus for the preparation of an alkylene glycol from the corresponding alkene.

BACKGROUND

Monoethylene glycol is used as a raw material in the manufacture of polyester fibres, polyethylene terephthalate (PET) plastics and resins. It is also incorporated into automobile antifreeze liquids.

Monoethylene glycol is typically prepared from ethylene oxide, which is in turn prepared from ethylene. Ethylene and oxygen are passed over a silver oxide catalyst, typically at pressures of 10-30 bar and temperatures of 200-300° C., producing a product stream comprising ethylene oxide, carbon dioxide, ethylene, oxygen and water. The amount of ethylene oxide in the product stream is usually between about 0.5 and 10 weight percent. The product stream is supplied to an ethylene oxide absorber and the ethylene oxide is absorbed by a re-circulating solvent stream containing mostly water. The ethylene oxide-depleted stream is partially or entirely supplied to a carbon dioxide absorption column wherein the carbon dioxide is at least partially absorbed by a re-circulating absorbent stream. Gases that are not absorbed by the re-circulating absorbent stream are recombined with any gases bypassing the carbon dioxide absorption column and are recycled to the ethylene oxide reactor.

The solvent stream leaving the ethylene oxide absorber is referred to as fat absorbent. The fat absorbent is supplied to an ethylene oxide stripper, wherein ethylene oxide is removed from the fat absorbent as a vapour stream. The ethylene oxide-depleted solvent stream is referred to as lean absorbent and is re-circulated to the ethylene oxide absorber to absorb further ethylene oxide.

The ethylene oxide obtained from the ethylene oxide stripper can be purified for storage and sale or can be further reacted to provide ethylene glycol. In one well-known process, ethylene oxide is reacted with a large excess of water in a non-catalytic process. This reaction typically produces a glycol product stream consisting of almost 90 weight percent monoethylene glycol, the remainder being predominantly diethylene glycol, some triethylene glycol and a small amount of higher homologues. In another well-known process, ethylene oxide is catalytically reacted with carbon dioxide to produce ethylene carbonate. The ethylene carbonate is subsequently hydrolysed to provide ethylene glycol. Reaction via ethylene carbonate significantly improves the selectivity of ethylene oxide conversion to monoethylene glycol.

Efforts have been made to simplify the process for obtaining ethylene glycol from ethylene, reducing the equipment that is required and reducing the energy consumption. GB 2107712 describes a process for preparing monoethylene glycol wherein the gases from the ethylene oxide reactor are supplied directly to a reactor wherein ethylene oxide is converted to ethylene carbonate or to a mixture of ethylene glycol and ethylene carbonate.

EP 776890 describes a process wherein the gases from the ethylene oxide reactor are supplied to an absorber wherein the absorbing solution mainly contains ethylene carbonate and ethylene glycol. The ethylene oxide in the absorbing solution is supplied to a carboxylation reactor and allowed to react with carbon dioxide in the presence of a carboxylation catalyst. The ethylene carbonate in the absorbing solution is subsequently supplied, with the addition of water, to a hydrolysis reactor and subjected to hydrolysis in the presence of a hydrolysis catalyst.

EP 2178815 describes a reactive absorption process for preparing monoethylene glycol wherein the gases from the ethylene oxide reactor are supplied to an absorber and the ethylene oxide is contacted with lean absorbent comprising at least 20 wt % water in the presence of one or more catalysts that promote carboxylation and hydrolysis and the majority of the ethylene oxide is converted to ethylene carbonate or ethylene glycol in the absorber.

Towers or columns allowing the intimate gas-liquid contacting required for such absorption are well known in the art and are referred to, for example, as fractionation, distillation or absorption towers. Such towers or columns contain trays stacked vertically through the column and are designed to conduct liquids in a zig-zag course downwardly through the column while admitting gases upwardly into horizontal-flowing portions of the liquid for intimate contact with the liquid.

Trays for providing the horizontal flow of the liquid are well known in the art and have been widely used. A tray generally comprises a perforated gas-liquid contacting member or members for effecting intimate contact between a gas rising through the tray and a liquid flowing across the surface of the tray across the perforated member. The perforated gas-liquid contacting member is in some instances provided with bubble caps or valves. At one edge of the contacting member of the tray is a liquid inlet area for receiving the liquid onto the tray. This area will generally contain no perforations. At the opposite edge of the contacting member is the liquid discharge end or region of the tray, which is provided with an outlet weir member extending vertically above the surface of the tray. The flowing liquid overflows the outlet weir for discharge from the tray. Accordingly, this outlet weir, maintains a given liquid depth on the tray.

Extending below the trays is one or more downcomer elements which, in cooperation with the inner surface of wall of column or tower, forms a downcomer for the passage of liquid downwardly from the tray liquid discharge region or end to the liquid inlet region of the vertically adjacent tray directly below. The downwardly flowing liquid received on the liquid inlet region or area then flows across the surface of this tray in a path across the perforated gas-liquid contacting member, to the tray discharge end or region and is discharged from the tray, over the outlet weir into the next downcomer.

A gas flows upwardly in the column through the perforations of the gas-liquid contacting members of the trays, allowing intimate contact with the liquid flowing horizontally across the surface of the tray. The gas is prevented from passing up the downcomers, as the downcomer element also functions as a baffle extending below the surface level of the flowing liquid to seal the downcomers from gas bypass. However, gas bypassing through downcomers may occur during startup of the process, when the column is not yet sufficiently filled with liquid.

In this reactive absorber system, there is an amount of unreacted alkylene oxide in the fat absorbent near the bottom of the absorption section of the column. In the downstream sections of this process, a large fraction of any remaining alkylene oxide will vaporize and be recycled back into the process. In addition, ethylene oxide that is present in the downstream section, which is operated at a higher temperature than the absorber, could negatively affect the selectivity of the process to monoethylene glycol. It is preferable to convert the alkylene oxide to alkylene carbonate as fully as possible before it reaches the downstream sections of the process.

It would be desirable to provide an improved process for the manufacture of alkylene glycol from an alkene. The present inventors have sought to provide a process and an absorption system that provides for a more complete conversion of alkylene oxide to alkylene carbonate within the reactive absorber.

SUMMARY OF THE INVENTION

The invention provides a process for the preparation of an alkylene glycol from an alkene comprising steps of: a) supplying a gas composition comprising alkylene oxide, alkene, oxygen, carbon dioxide and water vapour to an alkylene oxide absorber through a gas inlet, the absorber comprising an absorption section of vertically stacked trays and a sump at the bottom of the absorber, and allowing the gas composition to pass upwards through the absorption section; b) supplying a lean absorbent to the top of the absorption section and allowing the lean absorbent to pass downwards through the absorption section; c) intimately contacting the gas composition with lean absorbent on the trays in the absorption section in the presence of one or more catalysts that promote carboxylation and hydrolysis; and d) withdrawing fat absorbent from the absorption section and passing the fat absorbent and any liquid condensate that may be present in the gas composition through the sump, wherein the sump comprises one or more baffles that define a flow pathway from a sump inlet to a sump outlet between the one or more baffles. Within the present specification, the bottom wall of the sump is not considered as one of the one or more baffles in the sump in accordance with the present invention.

The invention also provides an absorber apparatus for the reactive absorption of a gas composition comprising alkylene oxide, alkene, oxygen, carbon dioxide and water vapour comprising an absorption section containing vertically stacked trays and a sump, wherein the absorption section has i) an inlet for liquid lean absorbent at the top of the absorption section, ii) an inlet for the gas composition below the absorption section, iii) a tray for collecting fat absorbent above the sump and iv) an outlet for unabsorbed gas at the top of the absorption section; and wherein the sump has i) a sump inlet for fat absorbent from the absorption section and any liquid condensate, ii) a sump outlet for fat absorbent, and iii) one or more baffles which are positioned in the sump to create a flow pathway from the sump inlet to the sump outlet between the one or more baffles.

DETAILED DESCRIPTION

The invention provides a process and an apparatus for the preparation of an alkylene glycol. Alkylene glycols are generally produced from the corresponding alkylene as set out below:

$R^1$, $R^2$, $R^3$ and $R^4$ are preferably chosen from hydrogen or an optionally substituted alkyl group having from 1 to 6 carbon atoms, more preferably from 1 to 3 carbon atoms. As substituents, moieties such as hydroxy groups may be present. Preferably, $R^1$, $R^2$ and $R^3$ represent hydrogen atoms and $R^4$ represents hydrogen or a non-substituted C1-C3-alkyl group and, more preferably, $R^1$, $R^2$, $R^3$ and $R^4$ all represent hydrogen atoms.

Examples of suitable alkylene glycols therefore include ethylene glycol and propylene glycol. In the present invention the most preferred alkylene glycol is ethylene glycol. In the present invention, the gas composition comprising alkylene oxide, alkene, oxygen, carbon dioxide and water vapour is preferably derived from the reactor product of an alkylene oxide reactor, in which an alkene is reacted with oxygen in the presence of a catalyst in a reactor to form alkylene oxide. In such a reaction, the oxygen may be supplied as oxygen or as air but is preferably supplied as oxygen. Ballast gas, for example methane or nitrogen, is typically supplied to allow operation at high oxygen levels without causing a flammable mixture. A moderator, e.g. monochloroethane or dichloroethane, may be supplied for ethylene oxide catalyst performance control. The alkene, oxygen, ballast gas and moderator are preferably supplied to recycle gas that is supplied to the alkylene oxide reactor from the alkylene oxide absorber (optionally via a carbon dioxide absorption column).

The alkylene oxide reactor is typically a multi-tubular, fixed bed reactor. The catalyst is preferably finely dispersed silver and optionally promoter metals on a support material, for example, alumina. The reaction is preferably carried out at pressures of greater than 1 MPa and less than 3 MPa and temperatures of greater than 200° C. and less than 300° C. The gas composition from the alkylene oxide reactor is preferably cooled in one or more coolers, preferably with generation of steam at one or more temperature levels.

The gas composition comprising alkylene oxide, alkene, oxygen, carbon dioxide and water vapour is supplied to an alkylene oxide absorber comprising an absorption section of vertically stacked trays. The trays provide a surface area for the absorbent and gas composition to come into contact, facilitating mass transfer between the two phases. Additionally, trays provide considerable liquid volume in which the liquid phase reaction can occur.

Each of the vertically stacked trays in the absorption section comprises a perforated gas-liquid contacting member or members, a liquid inlet area, an outlet weir area extending vertically above the surface of the tray at the opposite end of the tray from the liquid inlet area and a downcomer element. The downcomer element, in cooperation with the inner surface of wall of the absorption section, forms a downcomer for the passage of liquid downwardly to the liquid inlet region of the vertically adjacent tray directly below. In embodiments of the invention wherein the absorption section is of a large size, there may be more than one liquid inlet area, more than one outlet weir and more than one downcomer element per tray.

The reaction speed of the reactive absorption process for the conversion of alkylene oxide to alkylene glycol is relatively slow and, therefore, requires a large liquid hold up within the absorption section. The outlet weir on each tray is preferably at least 250 mm, more preferably at least 350 mm, even more preferably at least 400, yet even more preferably at least 500, most preferably at least 600 mm in height. The outlet weirs are at most 1500 mm in height, preferably at most 1000 mm, more preferably at most 800 mm in height.

The distance between two consecutive trays in a column is termed the plate spacing. The space between the top of a weir and the tray directly above it, termed 'vapour space' herein, can be calculated as the plate spacing minus the weir height and is preferably at least 150 mm, more preferably at least 200 mm. The vapour space is preferably no more than 1000 mm, more preferably no more than 500 mm.

The gas composition is supplied through a gas inlet below the absorption section and passes upwards through the trays. Liquid lean absorbent is supplied at or near the top of the absorber and the liquid flows downwards from tray to tray. The lean absorbent is preferably supplied to the uppermost tray in the absorption section. In another embodiment, the lean absorbent is supplied such that there are trays above the point at which the lean absorbent is supplied to the alkylene oxide absorber. In this embodiment, cold water or additional lean absorbent that has been cooled can be supplied at the top of the alkylene oxide absorber to absorb alkylene oxide or contaminants in the top of the alkylene oxide absorber.

The number of trays present in the absorption section will be dependent on the weir height and the amount of liquid hold up required in the absorption section. Preferably, the absorption section comprises at least 20 trays, more preferably at least 30 trays. Preferably the absorption section comprises less than 100 trays, more preferably less than 70 trays, most preferably less than 50 trays. More trays increase the absorption ability and reaction volume of the absorption section for any given weir height, but adding additional trays increases the size of the absorption section and therefore increases the expense involved in building and running it.

The gas composition is intimately contacted with lean absorbent on the trays in the alkylene oxide absorber in the presence of one or more catalysts that promote carboxylation and hydrolysis. If this occurs in the presence of only one catalyst, then the catalyst must promote carboxylation and hydrolysis. If this occurs in the presence of two or more catalysts, then each catalyst can promote carboxylation or hydrolysis or can promote both reactions (provided that at least one catalyst promotes carboxylation and at least one catalyst promotes hydrolysis). In a preferred embodiment the gas composition is contacted with lean absorbent in the presence of at least two catalysts including a first catalyst that promotes carboxylation and a second catalyst that promotes hydrolysis.

In one embodiment of the invention, the one or more catalysts that promote carboxylation and hydrolysis is/are homogeneous, and the lean absorbent comprises the one or more catalysts. Homogeneous catalysts that are known to promote carboxylation include alkali metal halides such as potassium iodide and potassium bromide, and halogenated organic phosphonium or ammonium salts such as tributylmethylphosphonium iodide, tetrabutylphosphonium iodide, triphenylmethylphosphonium iodide, triphenylpropylphosphonium bromide, triphenylbenzylphosphonium chloride, tetraethylammonium bromide, tetramethylammonium bromide, benzyltriethylammonium bromide, tetrabutylammonium bromide and tributylmethylammonium iodide. Homogeneous catalysts that are known to promote hydrolysis include basic alkali metal salts such as potassium carbonate, potassium hydroxide and potassium bicarbonate, or alkali metal metallates such as potassium molybdate. Preferred homogeneous catalyst systems include a combination of potassium iodide and potassium carbonate, and a combination of potassium iodide and potassium molybdate.

In another embodiment of the invention, the one or more catalysts that promote carboxylation and hydrolysis is/are heterogeneous and the heterogeneous catalyst(s) are contained in the vertically stacked trays. Heterogeneous catalysts that promote carboxylation include quaternary ammonium and quaternary phosphonium halides immobilized on silica, quaternary ammonium and quaternary phosphonium halides bound to insoluble polystyrene beads, and metal salts such as zinc salts immobilised on solid supports containing quaternary ammonium or quaternary phosphonium groups, such as ion exchange resins containing quaternary ammonium or quaternary phosphonium groups. Heterogeneous catalysts that promote hydrolysis include metallates immobilised on solid supports, for example molybdates, vanadates or tungstates immobilised on ion exchange resins containing quaternary ammonium or quaternary phosphonium groups, or basic anions such as bicarbonate ions immobilised on solid supports, for example bicarbonate immobilised on ion exchange resins containing quaternary ammonium or quaternary phosphonium groups.

In the embodiment wherein the gas composition is contacted with lean absorbent in the presence of at least two catalysts including a first catalyst that promotes carboxylation and a second catalyst that promotes hydrolysis, the ratio of first catalyst to second catalyst can be adjusted in order to vary the amount of carbon dioxide that is consumed or released in the alkylene oxide absorber. Preferably the gases from the alkylene oxide absorber are partially or entirely supplied to a carbon dioxide absorption column wherein the carbon dioxide is at least partially absorbed by a recirculating absorbent stream. By controlling the amount of carbon dioxide that is consumed or released in the alkylene oxide absorber, the capacity and cost of a carbon dioxide absorber column can be reduced.

The lean absorbent comprises at least 5 wt % water. The water that is present in the lean absorbent is used in the hydrolysis of alkylene oxide and alkylene carbonate that occurs in the alkylene oxide absorber. Preferably, the lean absorbent comprises at least 10 wt % water, more preferably at least 15 wt % water, most preferably at least 20 wt % water. Preferably the lean absorbent comprises less than 80 wt % water, more preferably no more than 50 wt % water, even more preferably no more than 30 wt % water. Higher levels of water in the lean absorbent may still provide good selectivity and catalyst performance, but higher quantities of water require additional water removal, with associated energy and equipment costs. The lean absorbent may also comprise alkylene glycol.

The temperature in the alkylene oxide absorber is preferably from 50° C. to 160° C., preferably from 80° C. to 150° C., more preferably from 80 to 120° C. This is higher than the temperature in an absorber in a conventional process and is required to promote the carboxylation and hydrolysis reactions. Temperatures higher than 160° C. are not preferred as this may reduce the selectivity of the alkylene oxide conversion to alkylene glycol. Both the gas composition comprising alkylene oxide, alkene, oxygen, carbon dioxide and water vapour and the lean absorbent are preferably supplied to the alkylene oxide absorber at temperatures in the range from 50° C. to 160° C.

The pressure in the alkylene oxide absorber is from 1 to 4 MPa, preferably from 2 to 3 MPa. The preferred pressure is a compromise between lower pressures that require less expensive equipment (e.g. equipment having thinner walls) and higher pressures that increase absorption and reduce the volumetric flow of the gas, thereby reducing the size of equipment and piping.

At least 50% of the alkylene oxide entering the alkylene oxide absorber is converted in the alkylene oxide absorber. Preferably, at least 60%, more preferably at least 70%, even more preferably at least 80%, most preferably at least 90% of the alkylene oxide entering the alkylene oxide absorber is converted in the alkylene oxide absorber. The alkylene oxide may undergo carboxylation, providing alkylene carbonate. The alkylene oxide may undergo hydrolysis, providing alkylene glycol. Additionally, the alkylene carbonate that is produced from the alkylene oxide may undergo hydrolysis, providing alkylene glycol.

Preferably, in the present invention, the alkylene oxide absorber forms part of a reaction system and process for the production, isolation and purification of alkylene glycol from alkylene via the corresponding alkylene oxide such as those described in EP 2178815 and similar. It will readily be understood that the absorber will be integrated into such a system which will contain a number of reactor vessels, columns and recycle streams.

The gas composition comprising alkylene oxide, alkene, oxygen, carbon dioxide and water vapour that is supplied to the alkylene oxide absorber comprises carbon dioxide. It is possible that the gas composition may contain insufficient carbon dioxide to achieve desired levels of carboxylation. An additional source of carbon dioxide is preferably supplied to the alkylene oxide absorber, e.g. recycle carbon dioxide from a finishing reactor, carbon dioxide from a carbon dioxide recovery unit or, at start-up, carbon dioxide from an external source. The ratio of the total amount of carbon dioxide supplied to the alkylene oxide absorber to the amount of alkylene oxide supplied to the alkylene oxide absorber is preferably between 5:1 and 1:3, more preferably between 3:1 and 3:5, most preferably between 3:1 and 4:5. A higher quantity of carbon dioxide improves the selectivity of the process because most alkylene oxide reacts with carbon dioxide to alkylene carbonate, which is subsequently hydrolysed to alkylene glycol and there is less opportunity for reaction between alkylene oxide and alkylene glycol to produce higher glycols. However, a higher quantity of carbon dioxide may also require additional removal capacity for carbon dioxide in the process and may also lead to a higher level of by-product formation. Alternatively, operating a connected alkylene oxide reactor with a recycled gas stream containing the excess carbon dioxide may adversely affect the catalyst performance.

Gases that are not absorbed in the alkylene oxide absorber are preferably partially or entirely supplied to a carbon dioxide absorption column wherein the carbon dioxide is at least partially absorbed by a recirculating absorbent stream. Gases that are not absorbed by the recirculating absorbent stream are preferably recombined with any gases bypassing the carbon dioxide absorption column and are recycled to the alkylene oxide reactor. Preferably the gases are cooled prior to recycle to the alkylene oxide reactor to reduce the water content. The water removed from the gas stream can optionally be recirculated to the alkylene oxide absorber. The performance of the catalyst in the alkylene oxide reactor may be detrimentally affected by an excess of water.

If the one or more catalysts that promote carboxylation and hydrolysis include a halogen-containing catalyst (e.g. an alkali metal halide, a halogenated organic phosphonium or ammonium salt or a quaternary ammonium or quaternary phosphonium halide immobilized on a solid support), then gases that are recycled from the alkylene oxide absorber to the alkylene oxide reactor may comprise halide-containing impurities such as iodide-containing impurities or bromide-containing impurities. It is possible that the catalyst in the alkylene oxide reactor may be detrimentally affected by these impurities. Therefore, in this embodiment it is preferred that gases that are recycled from the alkylene oxide absorber to the alkylene oxide reactor are contacted with one or more purification adsorbents capable of reducing the quantity of halide-containing impurities (especially iodide-containing impurities or bromide-containing impurities) prior to contacting the catalyst in the alkylene oxide reactor. The one or more purification adsorbent may be located within the reactor tubes of the alkylene oxide reactor, within the alkylene oxide reactor upstream from the reactor tubes or separately upstream from the alkylene oxide reactor.

The fat absorbent at the bottom of the absorption section may still contain quantities of unreacted alkylene oxide. The fat absorbent may contain up to 5 wt % alkylene oxide or up to 2 wt % alkylene oxide. The unreacted alkylene oxide is preferably converted to alkylene carbonate or alkylene glycol before it is removed from the absorber.

The fat absorbent is sent from the absorber to a hydrolyser, which operates at a lower pressure and higher temperature than the absorber. The absorbent flashes in the hydrolyser and unconverted alkylene oxide will enter the vapor phase and not be converted into alkylene carbonate or alkylene glycol. The alkylene oxide will be recycled to the absorber gas inlet after passing through a compressor. Recycling alkylene oxide leads to higher concentrations of alkylene oxide in the compressor, which can be a safety risk, and higher concentrations of alkylene oxide in the absorber inlet which can require a larger absorber. In addition, any alkylene oxide that is removed with the condensate downstream of the compressor may react under thermal conditions which could result in byproduct formation. The alkylene oxide may react to form glycols and increase the chemical oxygen demand of the wastewater stream if the condensed stream is routed to wastewater as a bleed stream instead of being recovered.

According to the present invention, the fat absorbent is collected from the absorption section and passed through the sump of the absorber. The sump comprises one or more baffles that define a flow pathway from the sump inlet to the sump outlet. The flow pathway may be substantially similar to a plug flow reactor and provides for additional residence time such that the carboxylation and/or hydrolysis reactions can continue in the sump. By continuing the reaction in the sump, the amount of alkylene oxide in the fat absorbent can be reduced to less than 100 ppmw, and preferably less than 10 ppmw.

In one embodiment, the fat absorbent is collected on a tray under the gas inlet. The fat absorbent is then passed into the sump via the sump inlet. Any condensate that enters with the gas composition is also collected on the tray and routed to the sump.

In another embodiment, the fat absorbent is collected on a tray above the gas inlet. This prevents the fat absorbent from being entrained by the gas entering the absorber via the gas inlet. The fat absorbent is then passed from that tray to a sump inlet where it enters the sump. The fat absorbent may be passed through a pipe or by a downcomer section designed for this purpose. Any condensate that enters with the gas stream is also collected and passed to the sump via the sump inlet.

The sump has a tray, plate or other device at the top of the sump to prevent fat absorbent from bypassing the sump inlet and entering directly into the sump along the flow pathway. If the fat absorbent bypassed the sump inlet, then it would not be in the sump for the desired residence time. The tray at the top of the sump may be a chimney tray, preferably with extended caps to prevent liquid or condensate from the gas inlet from passing directly into the sump. The use of a chimney tray allows carbon dioxide and other gases produced in the carboxylation and hydrolysis reaction in the sump to be passed into the absorber.

The one or more baffles in the sump may be in any number of sizes and configurations that provide for a flow pathway with sufficiently increased residence time. The average residence time in the sump is from 5 minutes to 60 minutes, and preferably from 9 minutes to 45 minutes. The flow pathway preferably has one or more changes in direction. In one embodiment, the baffles may be perpendicular to the direct path between the sump inlet and the sump outlet. In another embodiment, the baffles are straight baffles forming a flow pathway between the sump inlet and the sump outlet. This type of baffles would create a serpentine flow path with a plurality of changes in the direction of the flow. In another embodiment, the baffles may form a spiral flow path. In another embodiment, the baffles form a series of concentric circles where the flow pathway moves towards the center of the sump or alternatively, from the center to the outside of the sump. In addition to these embodiments, there is a large number of options for different numbers and geometries of baffles that will provide an increased residence time in the sump, and in some cases, approximate plug flow between the sump inlet and the sump outlet. Plug flow means no mixing in axial (flow) direction (i.e. no back-mixing) but only in radial direction. Any of these embodiments may have a strip at the end of or at locations along the one or more baffles that is at an angle to the baffle. This strip prevents the formation of a slip stream over the baffles.

The fat absorbent, after passing through the sump, is passed from the absorber via the sump outlet. In one embodiment of the invention, at least a portion of the fat absorbent is supplied to one or more finishing reactors. The finishing reactors may include reactors suitable for carboxylation, hydrolysis or hydrolysis and carboxylation. The temperature in the one or more finishing reactors is typically from 100 to 200° C., preferably from 100 to 180° C. The pressure in the one or more finishing reactors is typically from 0.1 to 3 MPa.

In another embodiment, a heater may be located between the absorber and the one or more finishing reactors. The fat absorbent is passed through the heater to heat the stream to a temperature in the range of from 130 to 170° C. Due to the higher temperatures in the heater, any remaining alkylene oxide should be converted to alkylene carbonate or alkylene glycol. In upset conditions, there is a possibility of additional alkylene oxide in the fat absorbent that would be converted in this heater. Any unreacted alkylene oxide that reaches the downstream steps will flash and not react efficiently.

Carbon dioxide may be produced in the one or more finishing reactors or the preheater and is preferably separated from the product stream as it leaves the one or more finishing reactors and is optionally recycled to the reactive absorber.

The fat absorbent comprising alkylene glycol is supplied to a dehydrator. The stream that is supplied to the dehydrator preferably comprises very little alkylene oxide or alkylene carbonate, i.e. most of the alkylene oxide or alkylene carbonate has been converted to alkylene glycol prior to supply to the dehydrator column, either in the alkylene oxide absorber, in a preheater or in a finishing reactor. Preferably the molar ratio of alkylene glycol to alkylene oxide and alkylene carbonate (combined) in the stream supplied to the dehydrator column is greater than 90:10, more preferably greater than 95:5, most preferably greater than 99:1.

The dehydrator is preferably one or more columns, including at least one vacuum column, preferably operating at a pressure of less than 0.05 MPa, more preferably less than 0.025 MPa and most preferably about 0.0125 MPa.

The dehydrated product stream is purified to remove impurities and provide a purified alkylene glycol product stream. If the one or more catalysts are homogeneous catalysts, it will be necessary to separate the one or more catalysts from the dehydrated product stream, preferably in a flash vessel. The one or more homogeneous catalysts are preferably recombined with the lean absorbent and supplied to the alkylene oxide absorber.

Figure 1A:
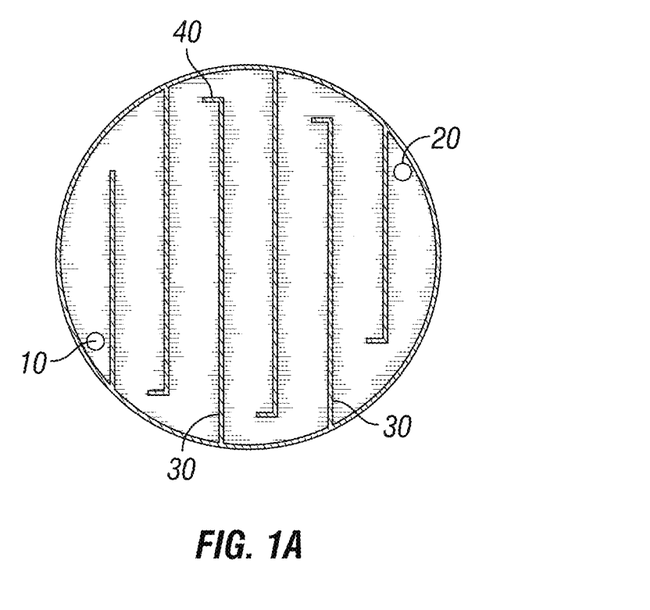
FIG. 1A depicts one embodiment of a baffle configuration in the sump.
Figure 1B:
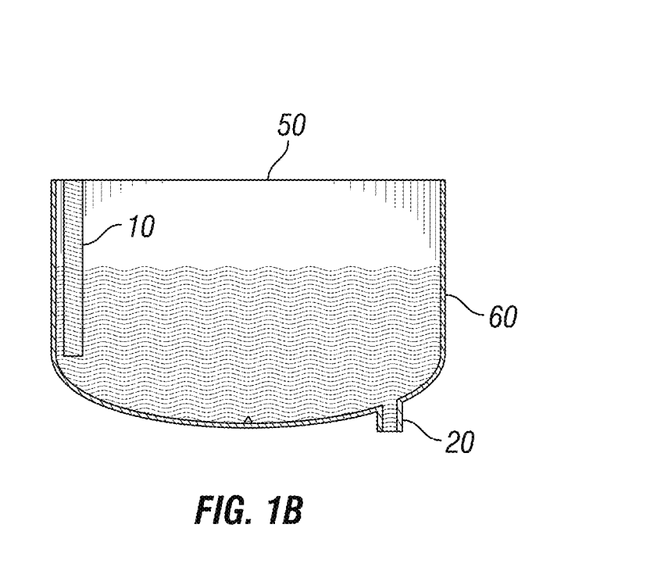
FIG. 1B depicts a cross-sectional view of the sump.

FIG. 1A depicts one embodiment of a baffle configuration in the sump. FIG. 1A shows a top view of the sump showing the sump inlet 10, the sump outlet 20 and the baffles 30. The baffles form a serpentine flow path from sump inlet 10 to sump outlet 20. Further, the additional strips 40 are shown on the end of each baffle. FIG. 1B shows a side view of the sump showing the sump inlet 10, sump outlet 20 and a tray 50 at the top of the sump 60.

Figure 2:
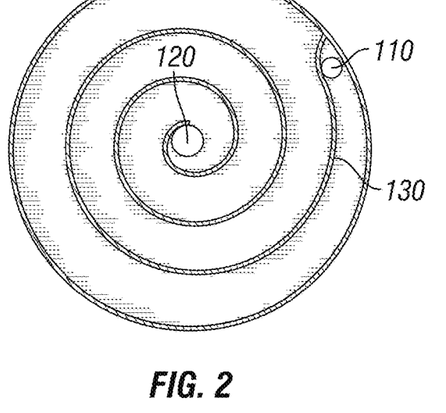
FIG. 2 depicts a further embodiment of a baffle configuration in the sump.

FIG. 2 depicts a further embodiment of a baffle configuration in the sump. FIG. 2 shows the sump inlet 110, the sump outlet 120 and a baffle 130 forming a spiral flow pathway.

Figure 3:
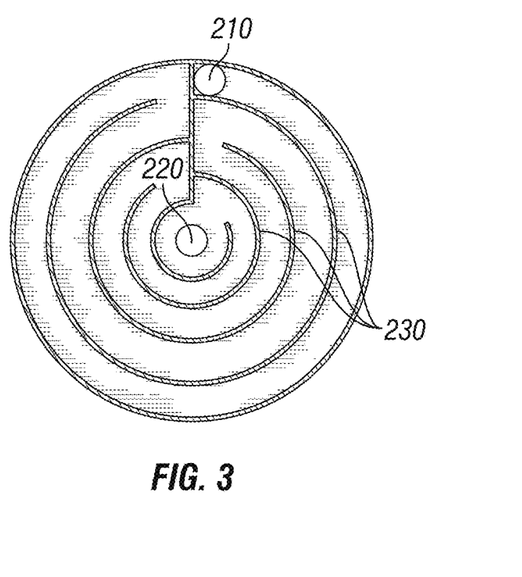
FIG. 3 depicts another embodiment of a baffle configuration in the sump.

FIG. 3 depicts another embodiment of a baffle configuration in the sump. FIG. 3 shows the sump inlet 210, the sump outlet 220 and the baffles 230 forming a series of concentric circles with openings to form a plurality of circular flow pathways between the sump inlet and the sump outlet.

Figure 4:
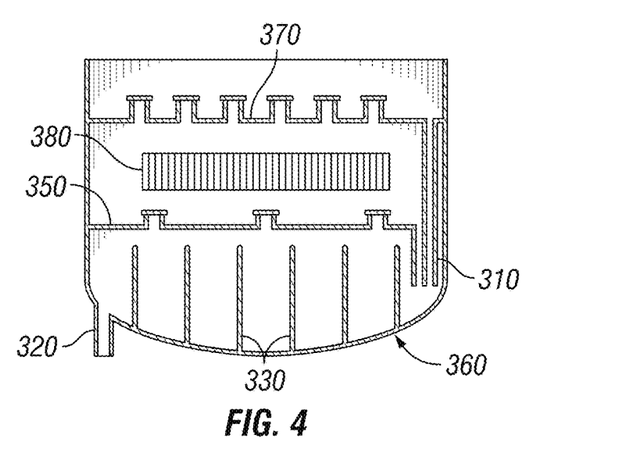
FIG. 4 depicts an embodiment of a portion of the absorber apparatus.

FIG. 4 depicts an embodiment of a portion of the absorber apparatus. The figure depicts the lower portion of the absorption section and the sump. The sump 360 comprises a plurality of baffles 330 arranged to create a flow pathway between the sump inlet 310 and the sump outlet 320. FIG. 4 shows a possible configuration for the tray 350 that separates the sump from the absorption section. The gas inlet 380 is positioned above the tray 350. In this embodiment, another tray 370 is positioned above the gas inlet to collect the fat absorbent. Tray 370 prevents liquid from falling directly on the gas inlet device which would result in entrainment of the liquid with the gas entering the absorber. The fat absorbent is collected on tray 370 and then passed to the sump inlet 310 via a downcomer, overflow weir, pipe or other type of conduit. Any condensate entering with the gas will collect on tray 350 and be routed to the sump via inlet 310.

Figure 5:
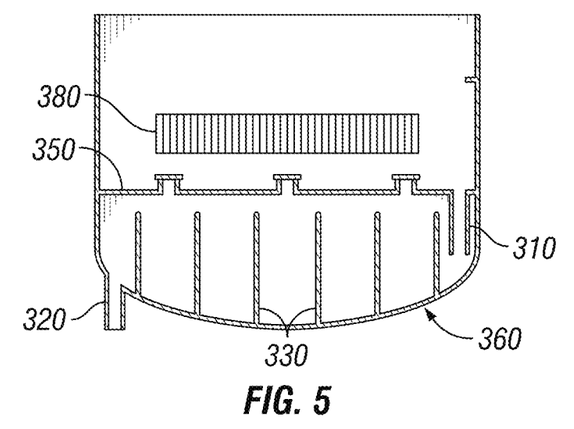
FIG. 5 depicts an embodiment of a portion of the absorber apparatus.

FIG. 5 depicts another embodiment of a portion of the absorber apparatus. The features shown in FIG. 5 operate in the same manner as the same features shown in FIG. 4. FIG. 5 shows an embodiment where the fat absorbent is collected on tray 350 along with any condensate from the feed. All of the liquid from tray 350 is then fed to the sump via sump inlet 310.

That which is claimed is:

1. An absorber apparatus for the reactive absorption of a gas composition comprising alkylene oxide, alkene, oxygen, carbon dioxide and water vapour comprising an absorption section containing vertically stacked trays and a sump, wherein the absorption section has
   i. an inlet for liquid lean absorbent at the top of the absorption section,
   ii. an inlet for the gas composition below the absorption section,
   iii. a tray for collecting fat absorbent above the sump and
   iv. an outlet for unabsorbed gas at the top of the absorption section; and
wherein the sump has
   i. a sump inlet for fat absorbent from the absorption section and any liquid condensate,
   ii. a sump outlet for fat absorbent, and
   iii one or more baffles which are positioned in the sump to create a flow pathway that approximate plug flow between the sump inlet to the sump outlet between the one or more baffles.

2. The apparatus of claim 1 wherein the tray for collecting fat absorbent is in direct fluid communication with the sump inlet.

3. The apparatus of claim 1 wherein the sump is separated from the absorption section by a plate or tray.

4. The apparatus of claim 3 wherein the tray is a chimney tray that has a sump inlet in the tray and a plurality of openings that allow for the passage of gas from the sump into the absorption section.

5. The apparatus of claim 1 having more than one baffle wherein the baffles are positioned parallel to each other or wherein the baffles are positioned to form a spiral.

6. The apparatus of claim 1 wherein at least one of the one or more baffles comprises a strip near the end of the baffle that is at an angle to the baffle.

7. The apparatus of claim 1 wherein the sump comprises at least two baffles.

\* \* \* \* \*